(12) United States Patent
Knuffman et al.

(10) Patent No.: US 10,020,156 B2
(45) Date of Patent: Jul. 10, 2018

(54) RESONANT ENHANCEMENT OF PHOTOIONIZATION OF GASEOUS ATOMS

(71) Applicant: ZEROK NANO TECH CORPORATION, Gaithersburg, MD (US)

(72) Inventors: Brenton J. Knuffman, Gaithersburg, MD (US); Adam V. Steele, Clarksburg, MD (US)

(73) Assignee: ZEROK NANOTECH CORPORATION, Gaithersburg, MD (US)

( * ) Notice: Subject to any disclaimer, the term of this patent is extended or adjusted under 35 U.S.C. 154(b) by 0 days.

(21) Appl. No.: 15/112,775

(22) PCT Filed: Jan. 15, 2015

(86) PCT No.: PCT/US2015/011626
§ 371 (c)(1),
(2) Date: Jul. 20, 2016

(87) PCT Pub. No.: WO2015/109105
PCT Pub. Date: Jul. 23, 2015

(65) Prior Publication Data
US 2016/0336139 A1    Nov. 17, 2016

Related U.S. Application Data

(60) Provisional application No. 61/929,348, filed on Jan. 20, 2014.

(51) Int. Cl.
*H01J 27/24* (2006.01)
*H01J 27/02* (2006.01)
(Continued)

(52) U.S. Cl.
CPC ............ *H01J 27/24* (2013.01); *H01J 27/022* (2013.01); *H01J 37/08* (2013.01); *G01N 27/64* (2013.01);
(Continued)

(58) Field of Classification Search
CPC .......... H01J 37/00; H01J 37/147; H01J 37/08; H01J 37/10; H01J 37/12; H01J 37/14;
(Continued)

(56) References Cited

U.S. PATENT DOCUMENTS

2008/0245964 A1*  10/2008  Miles ..................... G01N 22/00
                                                                    250/288
2008/0296483 A1   12/2008  McClelland
2012/0145919 A1*   6/2012  Steele .................... H01J 27/24
                                                                    250/424

OTHER PUBLICATIONS

Ryabtsev, et al., Collisional and Thermal Ionization of Sodium Rydberg Atoms: I. Experiment for nS and nD atoms with n=8-20.*
(Continued)

*Primary Examiner* — Jason McCormack
(74) *Attorney, Agent, or Firm* — Whiteford, Taylor & Preston, LLP; Peter J. Davis (57) ABSTRACT

A system and method for using a high-performance photoionization subsystem are disclosed. Embodiments of the present disclosure employ narrow bandwidth laser radiation to selectively excite ionizing resonant states of gaseous atoms in electric fields. This subsystem and method may be incorporated in an ion source producing ions by photoionizing gaseous atoms; the resultant ions may be employed to efficiently produce an ion beam of high brightness.

19 Claims, 6 Drawing Sheets

(51) Int. Cl.
*H01J 37/08* (2006.01)
*G01N 27/64* (2006.01)

(52) U.S. Cl.
CPC ............... *H01J 2237/0815* (2013.01); *H01J 2237/31701* (2013.01); *H01J 2237/31749* (2013.01)

(58) Field of Classification Search
CPC .. H01J 37/1472; H01J 37/1471; H01J 49/161; H01J 49/162
USPC ............. 250/396 R, 423 R, 424, 423 P, 288, 250/493.1, 492.1
See application file for complete search history.

(56) References Cited

OTHER PUBLICATIONS

Wolfgang Paul, ELectromagnetic Traps for Charged and Neutral Particles, Rev. Mod. Phys., vol. 62, No. 3, Jul. 1990, pp. 531-542.*
Ryabtsec, et al., Collisional and Thermal Isolation of Sodium Rydberg Atoms: I. Experiment for nS and nD atoms with n=8-20.*
Kime, L. et al. "High-flux monocrhamtic ion and electron beams based on laser-cooled atoms." Physical Review A. vol. 88, No. 3. Sep. 30, 2013.
European Search Report issued in corresponding European Application No. 15737044.6 dated Sep. 6, 2017.

* cited by examiner

*FIG. 6B*

RESONANT ENHANCEMENT OF PHOTOIONIZATION OF GASEOUS ATOMS

CROSS-REFERENCE TO RELATED APPLICATION

This application claims priority to U.S. Provisional Patent Application No. 61/929,348, filed Jan. 20, 2014, entitled "RESONANT ENHANCEMENT OF PHOTOIONIZATION OF GASEOUS ATOMS IN CHARGED PARTICLE SOURCES," which is incorporated herein by reference in its entirety.

BACKGROUND

Recently developed ion sources that produce ions from photoionized gases (collectively referred to herein as photoionized gas ion source—PIGIS), have the potential to offer superior brightness and reduced energy spread ion beams, when compared with alternative ion sources. These charged particle sources could find useful application in improving the performance of focused ion beam instrumentation in particular. A PIGIS is characterized by the use of photoionization of gaseous atoms to produce a source of charged particles and incorporates a photoionization subsystem having one or more beams of laser radiation that ionize gaseous atoms to form pairs of ion and electrons. Beams of both ions and electrons can be created by applying a constant electric field to the region in space in which the charged particles are created. The photoionization subsystem and method for configuring and applying such subsystem are herein referred to as the photoionization process.

The photoionization process is critical to the performance of a PIGIS. The utility of the PIGIS for focused ion beam applications can be enhanced if the photoionization process:
1) achieves a high ionization efficiency;
2) creates ions that may be formed into a beam with low chromatic energy spread;
3) creates ions that have a variance in their transverse velocities (relative to the beam's axis) that are substantially similar to that of the collection of cold neutral atoms from which the ions are created; and
4) suppresses the creation of more than one ion in close proximity to another.

Unfortunately, conventional photoionization systems are not designed to adequately meet the above criteria. Conventional photoionization systems may employ lasers with a photon energy substantially equal to the electric field-free ionization potential (FFIP) and are not configured to excite resonant structure in the photoionization spectrum. Conventional PIGISes are described in the references Knuffman, et al, titled "Nanoscale focused ion beam from laser-cooled lithium atoms" New J. Phys. 13 103035 (2011) and Reijnders, et al, titled "Low-Energy-Spread Ion Bunches from a Trapped Atomic Gas Phys. Rev. Lett. 102 034802 (2009).

SUMMARY

The present disclosure addresses the foregoing deficiencies in the art by providing a system and method for optimizing photoionization in PIGISes using resonances in the photoionization spectrum. In accordance with one embodiment of the present disclosure, a photoionization subsystem integrated into a system for producing ions in a PIGIS is provided. In this embodiment, the photoionization subsystem comprises a plurality of electrodes configured to generate a substantially controllable electric field having a magnitude and a direction. In this embodiment, the photoionization subsystem also comprises a population of atoms having a photoionizing resonance in the applied electric field. In this embodiment, the photoionization subsystem also comprises one or more beams of laser radiation, applied to at least a portion of said atoms, configured to ionize at least a portion of the atoms having laser radiation applied using the photoionizing resonance thereby producing ions. In this embodiment, the electric field may also be configured to accelerate the produced ions thereby forming a beam of ions. In this embodiment, the photoionization subsystem also comprises a vacuum chamber evacuated to less than about $10^{-6}$ millibar configured to contain at least the population of atoms, at least a portion of the electrodes, the portion of the beams of laser radiation that overlap with the atoms, and the produced beam of ions.

In accordance with another embodiment of the present disclosure, a method is provided for resonantly ionizing atoms to produce ions for a PIGIS is provided. In one embodiment, the method comprises providing an electric field having a direction in a region of space. In this embodiment, the method also comprises providing a population of atoms having a photoionizing resonance in the electric field in said region of space. In this embodiment, the method also comprises applying one or more beams of laser radiation to at least a portion of the atoms. In this embodiment, the method also comprises ionizing at least a portion of atoms having laser beams applied using the photoionizing resonance thereby producing ions. In one embodiment, the method comprises accelerating the ions to form a beam in the direction of the provided electric field. In one embodiment the method comprises providing a vacuum chamber evacuated to less than about $10^{-6}$ millibar configured to contain at least the population of atoms, at least a portion of the electrodes, the portion of the beams of laser radiation that overlap with the atoms, and the produced beam of ions.

These, as well as other features and benefits will become clear from a review of the following detailed description of illustrative embodiments and the accompanying drawings.

DETAILED DESCRIPTION

A system and method are described for resonant enhancement of photoionization of gaseous atoms in charged particle sources. As used herein, the term 'photoionized gas ion source' (PIGIS) refers to a source of ions that produces charged particles by photoionizing gaseous atoms for subsequent ion beam formation and manipulation, including focused ion beam applications and ion implantation. A PIGIS system includes a photoionization subsystem in which gaseous atoms are photoionized. In accordance with one embodiment of the present disclosure, this subsystem may be configured for resonant ionization in order to use of resonances in the photoionization spectrum to improve certain characteristics of the ion production and the performance of the resultant ion beam.

Figure 1:
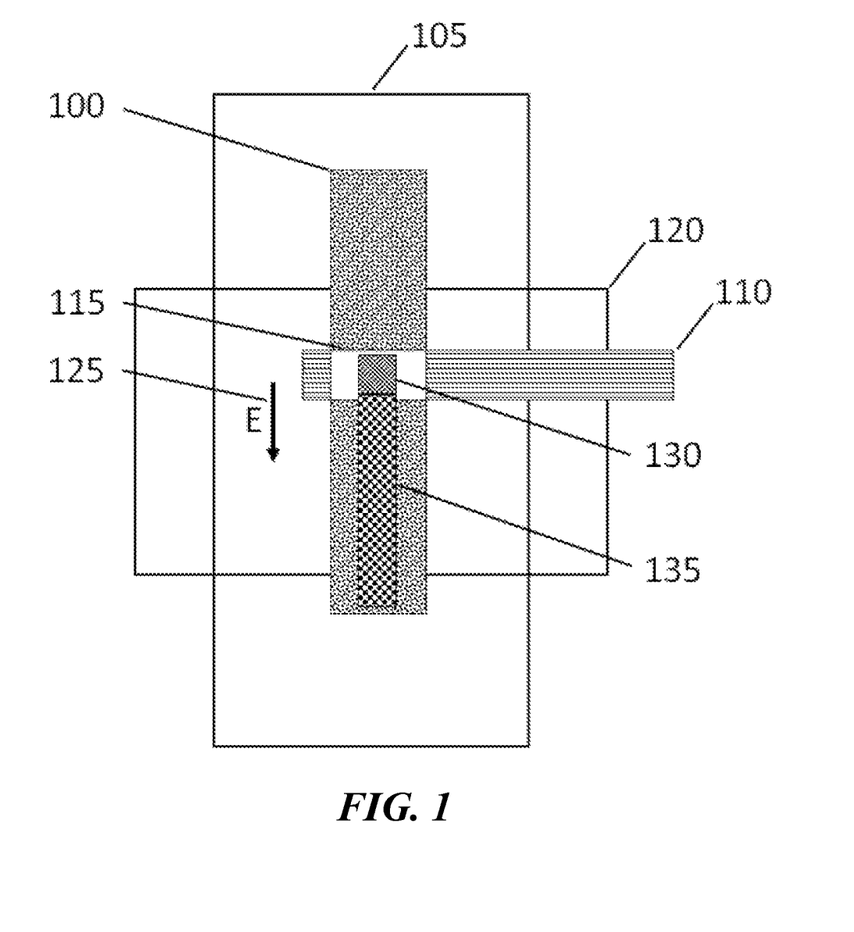
FIG. 1 shows a system for use in creating resonant enhancement of photoionization of gaseous atoms.

Referring now to FIG. 1, the photoionization subsystem configured for resonant ionization may contain population of gaseous atoms 100. The source of gaseous atoms may be contained within a vacuum chamber 105 evacuated to below $10^{-6}$ millibar (mbar). The actual pressure required may depend on the implementation.

The photoionization subsystem may also incorporate one or more beams of laser radiation 110, configured for resonant ionization. The beam or beams of laser radiation may be contained partially inside or outside the vacuum chamber 105. The beam or beams of laser radiation 110 may intersect the population of gaseous atoms 100 in a region defined as the photoionization region 115. The photoionization region 115 may be situated in relation to a plurality of electrodes 120 such that the electrodes 120 produce a controllable electric field 125 at the location of the photoionization region 115. The plurality of electrodes 120 may be contained partially inside or outside the vacuum chamber 105. The beams of laser radiation 110 may be configured to resonantly ionize a portion of the population of atoms 100 in the photoionization region 115 to produce a population of ions 130. The electric field 125 may produce a beam of ions 135 by accelerating the population of ions 130.

Figure 2:
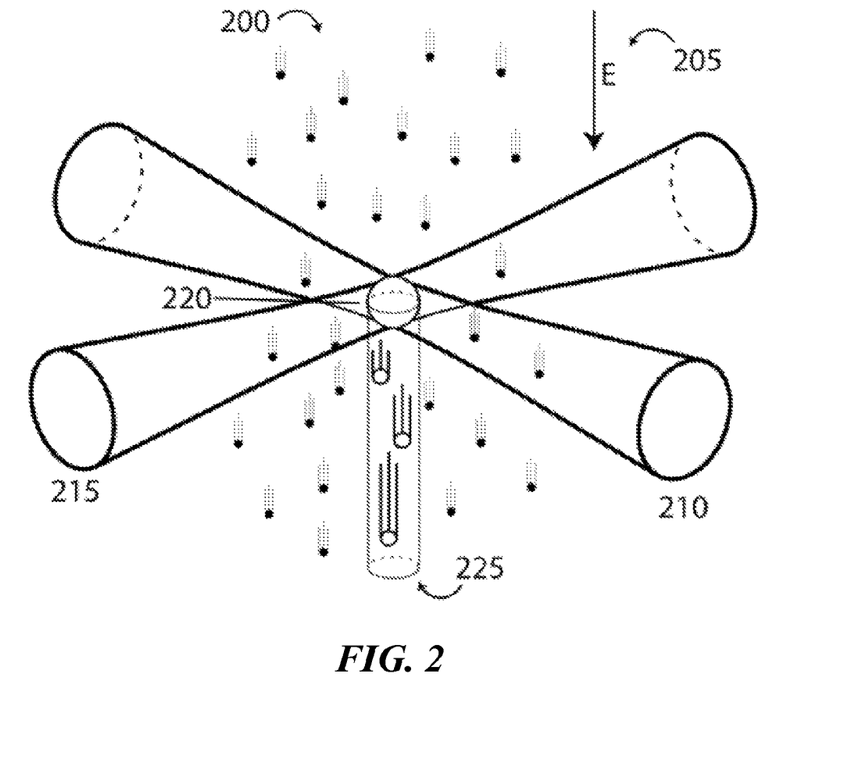
FIG. 2 illustrates a first embodiment of photoionization subsystem having a resonant laser excitation, a neutral atomic beam, an electric field and a resultant ion beam.

A first embodiment of the present disclosure is illustrated in FIG. 2. A beam of neutral cesium atoms with a longitudinal mean velocity of 10 m/s and a transverse temperature of approximately 30 µK is photoionized in an externally applied electric field 205 by a—first laser beam 210 and a second laser beam 215, both beams being focused and the intersection of which forms an ionization region 220. The first laser beam 210 is tuned to a strong internal Cs transition near 852 nm coupling a ground state to a first excited internal state. The second laser beam 215 can be tuned to a specific wavelength in the range from approximately 508 nm to 532 nm coupling the first excited internal state to a second resonantly-excited internal state that ionizes over time at a rate determined by the particular state. Upon ionization, the newly-created ions are accelerated under the influence of the electric field 205 to form a beam of ions 225.

Population of Atoms

In this first embodiment, the beam of neutral cesium atoms provides an ensemble of one or more atoms to a region of space between the pair of electrodes. In this first embodiment, the atoms are provided by a beam of neutral cesium atoms that have been laser-cooled, though the atoms could be provided by other means. Alternate methods may include collecting from a background vapor by a magneto-optical trap or delivering atoms via an atomic beam produced by an effusive oven with collimating apertures.

In this embodiment, the element used is cesium, though a number of other elements such as lithium, sodium, potassium, rubidium, cesium, magnesium, calcium, strontium, barium, chromium, erbium, silver, ytterbium, mercury, helium, neon, argon, krypton, and xenon could be used; this list is non-exhaustive. Photoionized gas ion sources may employ laser-cooling steps and would require the element to be one of those that can be laser-cooled. However, the method presented herein could be applied in systems where laser-cooling is not required. In this case, any element whose ionization spectra in an electric field contain resonances may be employed. In another embodiment, a molecular species whose ionization spectra in an electric field contain resonances may be employed in place of the atomic elemental species.

The Electric Field

In this first embodiment, an applied electric field is created by two electrodes that can have an adjustable voltage applied to them to create an electric field of configurable strength in the region where atoms are photoionized. In general the number of electrodes with voltages applied used to produce the electric field is not limited to two. When ionization occurs, the resultant positive ions are accelerated along the direction of the electric field axis forming an ion beam; In discussing quantities related to the system, it may be important to refer to those quantities defined along the direction of the applied electric field (herein referred to as longitudinal) and those defined perpendicular to the applied electric field (herein referred to as transverse).

Photoionization Region

To photoionize gaseous atoms in an electric field, one or more beams of laser radiation are required. The laser beam or beams overlap with at least a portion of the atoms provided to the region of space between the electrodes. The volume where the laser beams overlap with at least a portion of the atomic beam is referred to as the photoionization region. In this first embodiment, two laser beams are used. The power and frequency in one or more of the beams of laser radiation may be variable in time.

The photoionization region is maintained in an enclosure with a vacuum level of less than about $10^{-6}$ mbar. The enclosure contains the gaseous atoms being photoionized, at least a portion of the beam or beams of laser radiation, and at least a portion of the electrodes with voltages applied that create the applied electric field.

Resonant Photoionization

Atoms enter the photoionization subsystem in an initial state with a particular energy. One or more beams of laser radiation impart energy to the atoms required to remove an electron, i.e. photoionize the atom. If a photoionization resonance (described below) is used in the ionization process, it will be referred to as a resonant ionization process (RIP). If no photoionization resonance is used in the ionization process, it will be referred to as a nonresonant ionization process (nRIP).

The difference between the energy of the initial atomic state and the ionization potential (energy at which an electron becomes unbound from the atom) in the absence of an electric field is defined to be the field-free ionization potential (FFIP).

The photoionization resonances referred to in the present disclosure are found at energies less than the FFIP but typically greater than the so-called 'saddle point' energy, where ionization nominally becomes energetically allowed in the presence of an electric field as described in the book by Gallagher titled "Rydberg Atoms" Cambridge University Press (1994):

$$k = k_0 - \Delta k_F, \quad (1)$$

$$\Delta k_F = 2R_\infty \sqrt{E} \quad (2)$$

where k is the saddle point energy in wavenumbers, $k_0$ is the atom's FFIP in wavenumbers, $R_\infty$ is the Rydberg constant and E is the electric field in the photoionization region (in atomic units). It is noted that ionizing resonances with energy lower than the saddle point energy may be employed if the corresponding ionization rate is sufficiently high, as described in the section titled Low Chromatic Energy Spread.

Figure 3:
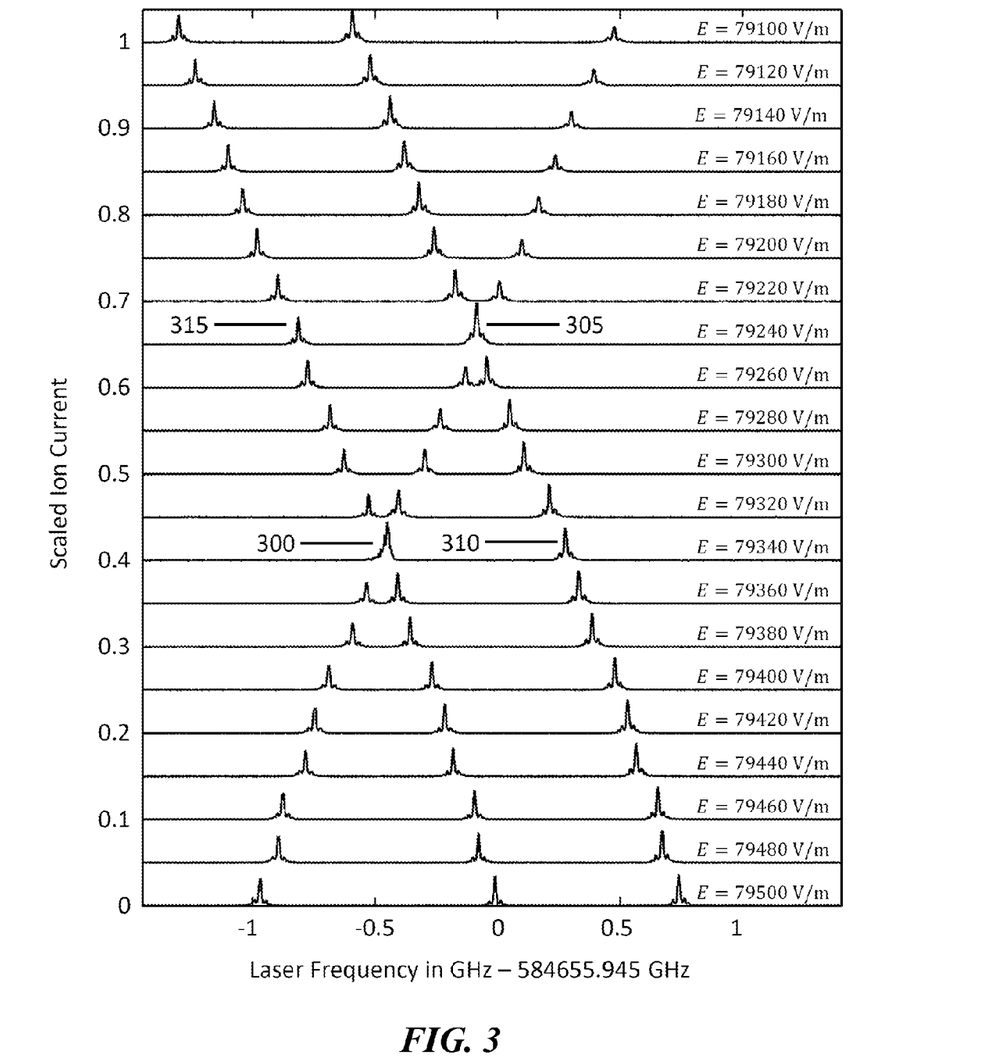
FIG. 3 shows spectra of photoionization resonances, plotting ion current vs. laser frequency for a variety of electric fields near 80 kV/m.

The ionization spectra in FIG. 3 show plots of ion current vs. laser frequency (of the second laser 215 shown in FIG. 2 with wavelength between 508 nm and 532 nm) for a variety of applied electric field strengths. These data were obtained in a test system (described below) implementing the first embodiment. As demonstrated in the figure, for a given applied electric field, photoionization spectra may contain a plurality of resonances. Additionally, for a particular electric field, the resonances in the ionization spectra may differ in number and amplitude and are excited at different laser frequencies. These spectra show only a portion of the excitable photoionization resonances. Resonance in the photoionization spectra have been described in the article by Littman, et al, titled "Field-Ionization Processes in Excited Atoms" Phys. Rev. Lett. 41, 103 (1978).

When choosing a particular resonance to use for ion production in beam applications, a number of properties may be considered. These properties may include ionization rate, excitation cross-section, momentum coupling to transverse degrees of freedom of the resultant ion and electron, dipole moment, and spectral width of the resonance feature. Criteria for selection of a resonance are discussed in more detail below in the context of measurements made in the test system.

In general, the atomic species and electric field strength determine configuration of the laser beam or beams required to excite a particular resonance in a RIP. Each atomic species may have a distinct set of ionizing resonances available in an electric field of a given strength. The frequency, power, and polarization of each beam of laser radiation may be configured so that collectively the laser beams act to excite at least a portion of the atoms from an initial state to an available quasi-bound excited state that will subsequently ionize over time at a given rate. The spectra in FIG. 3 show that the photo energy required to excite an ionizing resonance may depend on the magnitude of the applied electric field. This implies that an electric field with controllable magnitude may be tuned to shift the energy of the ionizing state substantially into resonance with the photo energy supplied by the laser radiation.

First, the frequencies of the laser beam or beams may be chosen or tuned such that the photo energy supplied by the beam(s) of laser radiation in transferring a single atom from the initial state to the ionizing state is substantially equal to the difference in energy between the initial and ionizing state. Alternatively, the electric field may be tuned to bring an ionizing state substantially into resonance with the photo energy supplied by the beams of laser radiation.

Second, the bandwidth of excitation should not substantially exceed the energy spacing between adjacent resonant features. When the bandwidth of excitation is substantially less than the spacing between adjacent features, those resonance features may be clearly resolved in a photoionization spectrum. If the bandwidth of excitation is significantly larger than the spacing between resonances, individual resonances may not be resolved in a photoionization spectrum. A list of factors that may affect the bandwidth of excitation in a typical system includes: the intrinsic atomic response to applied laser light, the frequency spectrum of applied laser light, and the intensity of applied laser light. In some cases, the spacing between two resonant features tends substantially to zero, as shown in FIG. 3 near the points labeled 300 and 305. These composite features are resolvable from the adjacent features labeled 310 and 315, respectively, and therefore do not constitute exceptions to the bandwidth requirement. In an embodiment of the present disclosure, the RIP may employ a composite feature that is resolvable from other adjacent features in the spectrum.

Third, the polarization of the laser beam or beams may be chosen to modulate the strength of a particular ionizing resonance. A particular choice of polarization may require more or less laser intensity in the laser beam or beams to excite an equivalent population of atoms. In some cases, the choice of polarization can substantially inhibit or substantially eliminate excitation of a particular ionizing resonance.

In the RIP in the first embodiment, a first laser beam couples the cesium atoms in the initial state $6S_{1/2}$ to a second bound internal state $6P_{3/2}$, the first beam of laser radiation having a photon energy substantially equal to the energy difference between the $6P_2$ state and the $6S_{1/2}$ state; a second laser then couples the second bound internal $6P_{3/2}$ state to an ionizing state, the second beam of laser radiation having a photon energy substantially equal to the energy difference between the ionizing state and the $6P_{3/2}$ state. The photon energy of the first beam of laser radiation plus the photon energy of the second beam of laser radiation is equal to the energy difference between the ionizing state and the initial $6S_{1/2}$ state. The frequencies and intensities of the beams of laser radiation employed in the excitation are not varied in time; each has an intrinsic bandwidth of less than 2 MHz. The laser intensities are configured to be lower than an amount that would cause excessive power broadening on either transition. Resonances in the ionization spectra are resolvable by incrementing the photon energy of the beam of laser radiation that couples the $6P_{3/2}$ state to the ionizing state. Thus in the first embodiment, the beams of laser radiation are configured to ionize atoms using an ionizing resonance.

In general, the laser beams may be configured to excite ionizing resonances in a multitude of ways for a given electric field and atomic species; the configuration is not restricted to the first embodiment described in the previous paragraph. As an alternative to the first embodiment, the first laser beam could be configured with a photon energy having a substantial detuning in energy from the difference between the $6P_{3/2}$ state and the $6S_{1/2}$ state, provided that the second laser beam has a photon energy that is adjusted by an amount equal in magnitude but opposite in sign to the detuning of the first laser beam. In this case, the total photon energy supplied by the beams of laser radiation is substantially equal to the difference between the energy of the initial state and that of an ionizing resonance, and the configuration may ionize atoms using the ionizing resonance.

Laser-frequency-stabilization techniques known in the art may be employed in embodiments of the invention described in the present disclosure.

Description of Example Embodiments

A test system was constructed to demonstrate the utility of the first embodiment. This system incorporates a PIGIS that includes the first embodiment of the RIP described above. The system also includes a beam formation system and a microchannel plate. The microchannel plate provides for measurements of the spatio-temporal characteristics of the created ion beam. Properties of the charged particle source may be inferred by these measurements and thereby show how the utility of the PIGIS is enhanced by the RIP.

A test system was constructed to demonstrate the four advantages enumerated in the background of the invention. These include a realization of enhanced ionization efficiency, formation of a low chromatic energy spread beam, and creation low transverse temperature ions and electrons. Data has also been collected showing the feasibility to suppress the excitation of adjacent particles.

Description of the Test System

Figure 4:
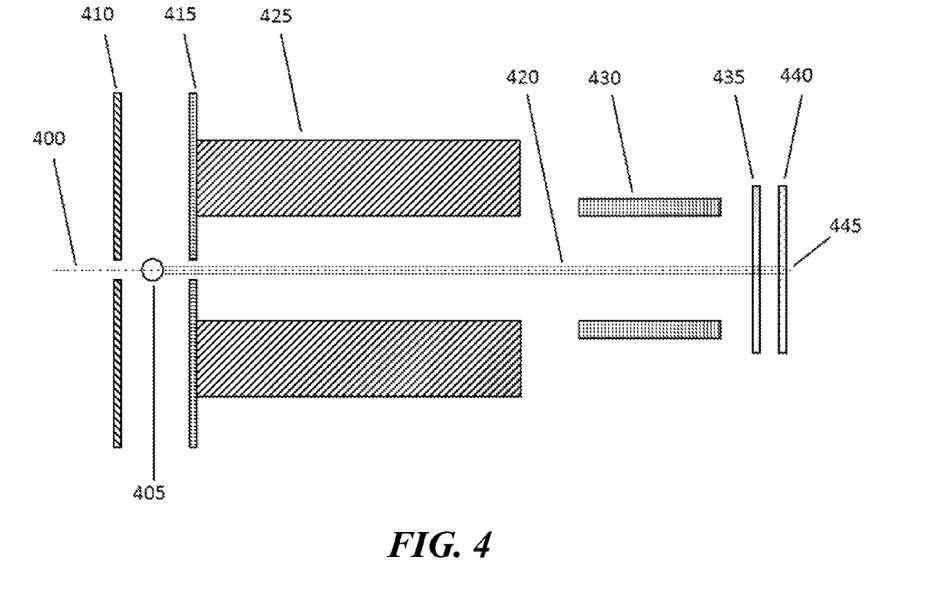
FIG. 4 illustrates a test system incorporating a low temperature charged particle source, beam formation subsystem, and micro channel plate measurement apparatus.

The PIGIS test system is described herein. The PIGIS utilizes either a RIP or an nRIP to generate ions or electrons. Referring now to FIG. 4 showing the PIGIS test system, the parts represented in the drawing are substantially symmetric about the symmetry axis 400. Charged particles created in the ionization volume 405 between the first electrode 410 and second electrode 415 are accelerated by an electric field to form a beam 420 which passes through an aperture in the second electrode 415. The beam 420 then travels through a resistive acceleration tube 425 where additional acceleration or deceleration may occur. As the beam 420 exits the tube, the beam 420 passes through a shield tube 430 and is directed towards a microchannel plate (MCP) 435 and phosphor screen 440 assembly. The MCP is capable of measuring the current density of the beam impinging upon it as well as the precise time of arrival of individual ions. An image of the spatial distribution of current 445 is visible on the phosphor screen 440.

Enhancement of Ionization Efficiency

Figure 5:
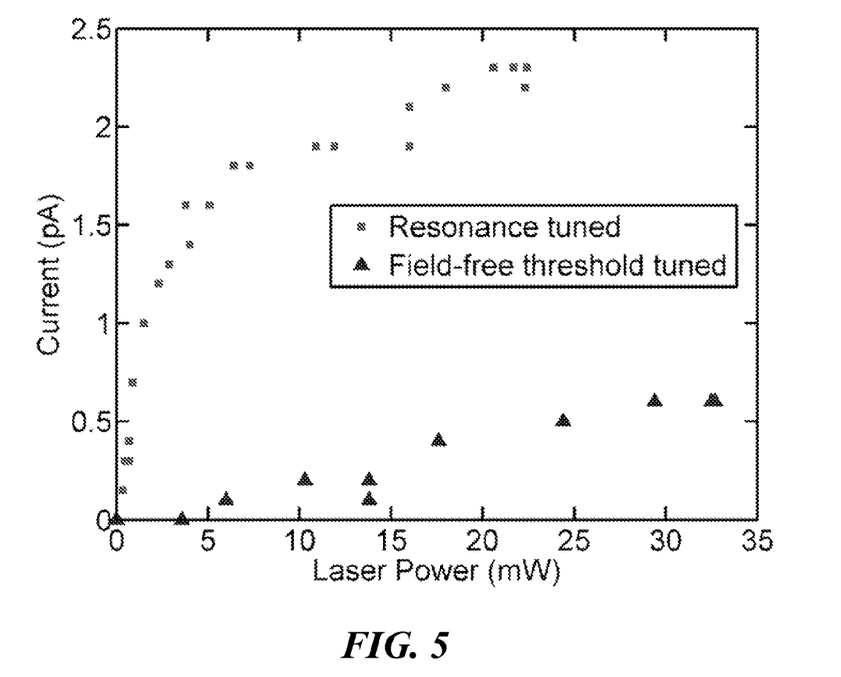
FIG. 5 illustrates a comparison of beam currents created in the test system, comparing a resonant photoionization process to nonresonant ionization process.

The RIP enables a reduction in the laser power required for efficient ionization; efficiency in this context means that neutral atoms entering the photoionization region are ionized with high probability. Highly efficient ionization occurs when the total photon energy of the RIP is tuned to couple the initial state to one of the quasi-bound states described above. The relative strength of a particular resonance, compared with an nRIP whose total photon energy is substantially equal to the FFIP, may be obtained by comparing the ratio of laser beam powers required to obtain equivalent beam currents. A test of this property of the RIP was performed by measuring the total beam current generated by the test system as a function of power in the second beam of laser radiation. Two data series where taken, one with the RIP's total photon energy tuned to a strong resonance in a field of 100 kV/m, and another with the nRIP total photon energy tuned to the FFIP in the same field. FIG. 5 shows the output current in the test system as a function of laser power. Comparison of the linear portions of FIG. 5 show that this resonance can achieve rates of ionization that would require 37 times more power in the second beam where it instead tuned so that the total photon energy was substantially equal to the FFIP.

Low Chromatic Energy Spread

Ions beams created by the PIGIS and lasers configured to excite a RIP were found to have energy spreads not substantially greater than an ion beam created from a PIGIS with employing a nRIP with lasers tuned to the FFIP.

The intrinsic energy spread of a PIGIS may be written:

$$\Delta U_0 = E \cdot \Delta z, \quad (1)$$

where $\Delta z$ is the size of the volume from which ions are being produced along the direction of the field E.

In addition to this intrinsic energy spread, ion beams created in PIGIS systems employing a RIP may have an additional contribution to their energy spread that arises because excited atoms evolve into ions in a variable length of time characterized by an exponentially decaying distribution having some lifetime $\tau$ associated with each excited state. This lifetime will add a chromatic energy spread to the beam according to the relation:

$$U_\tau \propto E \cdot v_z \cdot \tau, \quad (2)$$

where E is the field in the photoionization region, $v_z$ the axial velocity of the neutral atom beam, and $\tau$ the lifetime of the resonant state. If beams created with a RIP equipped system are to have a substantially similar energy spread to systems employing a nRIP, then $\Delta U_\tau$, should be kept much smaller than $\Delta U_0$.

The PIGIS test system was used to measure the lifetime of particular resonant states to which the RIP's lasers had been tuned. First, the second beam of laser radiation is pulsed on for approximately 50 ns, then left off for approximately 500 µs. The relative time at which ions arrive at the MCP was recorded. A histogram exhibiting the exponential decay from the excited state into the ion/electron pair can be built up from counting many such pulses. For appropriately set voltages on the test system electrodes the variance in time of flight owing to uncertainty in initial ion position is negligibly small. A best fit of a decaying exponential to this decay curve yields the value for the state's lifetime. The lifetime of the resonance used in the ionization efficiency data shown above was found to be less than 50 ns. For typical fields of $10^5$ V/m, axial ionization lengths of a few microns, and axial beam velocities of 10 m/s the energy spread contribution due to the lifetime of the excited state will add a negligibly to the ion beam's chromatic energy spread.

In an embodiment, a particular resonant feature may be selected from a group of resonant features of differing lifetimes, such that the lifetime does not contribute substantially to the energy spread of the ion beam.

Reduced Transverse Velocity Spread

The ionization process may affect the transverse temperature of the ion beam through electron-ion recoil as the electron and ion separate. When the photo energy was tuned to particular resonances it was found that the RIP will give rise to ions with a reduced transverse temperature, when compared to a similar system using an nRIP with total photon energy tuned to the FFIP. The reduced temperatures achievable by using a RIP may enhance the utility of the PIGIS.

The temperature of the ions can be inferred from a measurement of the transverse velocity distribution of the electrons created by the photoionization process. The test system was configured to utilize a RIP in a field of $10^5$ V/m; the RIP's total photon energy was tuned to the same resonance used in the examinations of ionization efficiency and energy spread above. This distribution of electron velocities was measured; this enables a calculation of the contribution to ion transverse velocity (and hence temperature) that will occur due to the photoionization process. This contribution can be found through conservation of momentum:

$$v_i = \left(\frac{m_e}{m_i}\right) v_e, \quad (3)$$

where $m_i$ and $m_e$ are the masses of the ion and electrons and $v_i$ and $v_e$ are the ion and electron velocities.

Figure 6A:
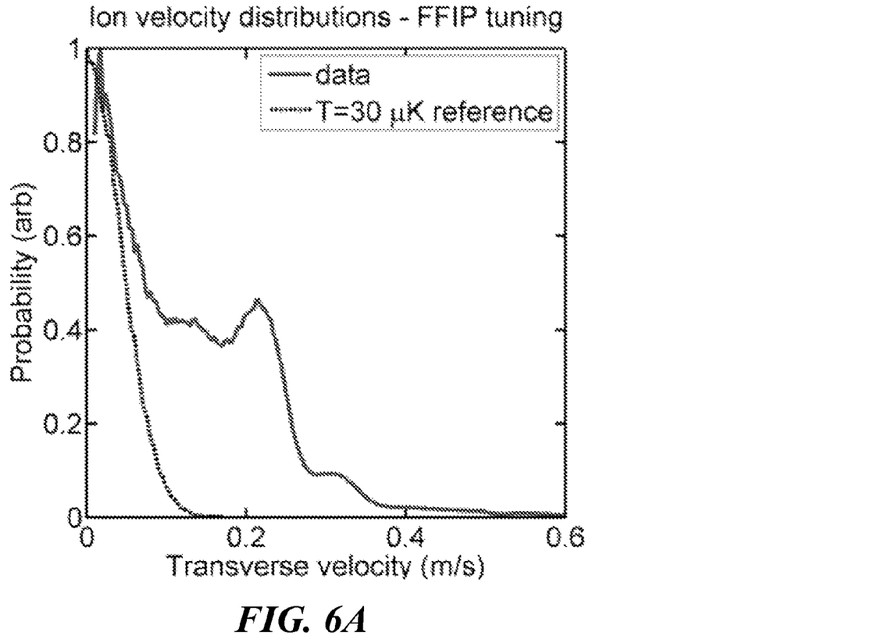
FIGS. 6A and 6B (referred to herein as FIG. 6) illustrates photoionization process contributions to ion beam transverse velocities, comparing a nonresonant ionization process in FIG. 6A to a resonant ionization process in FIG. 6B.
Figure 6B:
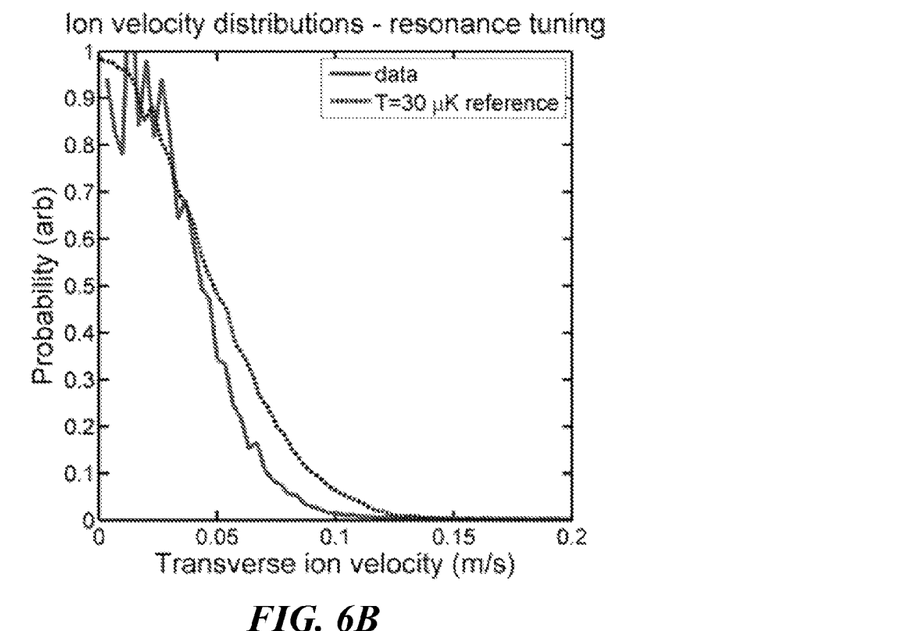

For a PIGIS that employs a RIP tuned to this particular resonance FIG. 6B shows that the photoionization process will not substantially increase the transverse temperature of the ions above 30 µK. This is apparent from a comparison of the width of the distribution of the inferred contribution to ion velocity gained through the photoionization process (solid line) with that of the 30 µK reference curve (dashed line). Similar or even superior performance may be achieved when the RIP is tuned to other resonances as well.

That the use of an RIP substantially enhances the utility of a PIGIS can be seen through a comparison of FIG. 6A with FIG. 6B. In FIG. 6A, the test system was configured to use an nRIP with total photon energy set to the FFIP. FIG. 6A, is the inferred contribution to ion velocity. In this case, the ion velocity would be substantially larger than 30 μK, even if the underlying neutral atom temperature was less than this.

In an embodiment, a particular resonant feature may be selected from a group of resonant features of differing electron-ion recoil properties, such that the recoil property does not contribute substantially to the transverse velocity spread of the resultant ion beam relative to the underlying thermal velocity spread inherited from the population of atoms. In another embodiment, the recoil imparted in the photoionization process may increase the velocity spread of ion beam relative to that inherited by the atoms while still imparting lower recoils than employing an nRIP with photo energy tuned to the FFIP. In this embodiment, a particular resonant feature may be selected from a group of resonant features of differing electron-ion recoil properties, such that the recoil property imparts a transverse velocity spread to the resultant ion beam that is substantially less than would be imparted by tuning the laser radiation to impart a photo energy that is substantially equal the FFIP.

Application of an Excitation Blockade

Use of a RIP may also enhance the utility of a PIGIS through its ability to reduce the probability of two charged particles being created in close proximity to each other when compared with a similar PIGIS using an nRIP. This effect may reduce the Coulomb interaction-based heating in the source and lead to an enhancement of brightness and the PIGIS's utility.

The use of certain resonances with a RIP will inhibit the generation of nearby charged particles by creating an excitation blockade in the PIGIS. Excitation blockade behavior typically arises from electrostatic multipole interactions among excited states of a multi-atom system. A number of embodiments may be conceived that employ various types of electrostatic multipolar interactions or combinations thereof, two of which are described in the following.

In one embodiment, the ionizing atomic states in electric fields excited in the RIP may exhibit large permanent dipole moments. These excited state atoms may have a significant dipole-dipole interaction energy at the separation length scales between atoms found in a high brightness PIGIS's ionization volume. This interaction strength may exceed the spectral width of the atomic resonance or laser linewidth (whichever is greater); in this case, the double excitation state may be out of resonance with twice the laser photon energy and may be excited with a lower probability than it would otherwise be, for instance in a PIGIS using an nRIP.

The feasibility of this technique was demonstrated by measurements performed in the test system. To estimate the relative strength of the blockade, measurements of the dipole moment of states were performed. This was done by tracking the change in RIP total photon energy required for maximally efficient ionization against small changes in electric field strength for particular resonances; the spectral width of said resonances were also measured. As an example, a state was identified with a dipole moment $$p = \left|\frac{\partial U}{\partial E}\right| = h \times 11 \text{ MHz}/Vm^{-1}$$

with a spectral width of $\Delta v = 14$ MHz. A simple estimate of the blockade radius, as described in an article by Vogt, et al, title "Electric-Field Induced Dipole Blockade with Rydberg Atoms" Phys. Rev. Lett. 99 073002 (2007), yields $R = \sqrt[3]{p^2/[4\pi\epsilon_0 h\Delta v]} \approx 4$ μm. This radius defines a volume in which multiple excitations may be inhibited. Since this volume is slightly larger than the size of the ionization volume, multiple simultaneous excitations should be suppressed in a PIGIS that employed a RIP tuned to this resonance. As a result, Coulomb effects leading to heating and a reduction in brightness would be lessened in such a system, enhancing the utility of the PIGIS.

In another embodiment, the Coulomb field from an ion may shift the resonant frequency required for a RIP in neighboring atoms by an amount greater than the larger of the atomic line or the linewidth of an ionizing laser, thereby reducing the probability of excitation in the neighboring atoms. In this case as well, the probability of creating ions nearby to one another is reduced, which may result in a reduction in adverse heating effects.

In an embodiment, a particular resonant feature may be selected from a group of resonant features of differing multipole interaction properties, such that the multipole interaction property is configured to substantially reduce the probability of multiple, substantially simultaneous excitations.

From the foregoing, it will be appreciated that specific embodiments of the disclosure and test systems have been described herein for purposes of illustration, but that various modifications may be made without deviating from the spirit and scope of the various embodiments of the disclosure. At least some embodiment can (1) provide a high ionization efficiency, (2) create ions that may be formed into a beam with desired (e.g., low chromatic energy spread), (3) create ions that have a variance in their transverse velocities (relative to the beam's axis) that are substantially similar to that of the collection of cold neutral atoms from which the ions are created, and/or (4) reduce or limit the creation of more than one ion in close proximity to another. Accordingly, while various advantages associated with certain embodiments of the disclosure have been described above in the context of those embodiments, other embodiments may also exhibit such advantages, and not all embodiments need necessarily exhibit such advantages to fall within the scope of the disclosure. The various aspects and embodiments disclosed herein are for purposes of illustration and are not intended to be limiting, with the true scope and spirit being indicated by the following claims.

What is claimed is:

1. A photoionization subsystem incorporated into a photoionized gas ion source, the subsystem comprising:
   a) a plurality of electrodes configured to generate a substantially controllable applied electric field having a magnitude and direction;
   b) a population of atoms having a photoionizing resonant frequency specific to said applied electric field;
   c) one or more beams of laser radiation, applied to at least a portion of said atoms;
   d) said laser beam or beams of radiation tuned to a frequency that corresponds to said photoionizing resonant frequency of at least a portion of the atoms whereby said at least a portion of the atoms are excited from a ground state to a quasi-bound excited state that will subsequently ionize over time at a given rate thereby producing ions, said laser beam or beams of radiation having a total photon energy less than a field-free ionization potential of said population of atoms;

e) said electric field configured to accelerate the ions thereby forming a beam of ions; and f) a vacuum chamber evacuated to less than about $10^{-6}$ millibar, said vacuum chamber configured to contain at least the population of atoms, at least a portion of the electrodes, the portion of the beams of laser radiation that overlap with said population of atoms, and the beam of ions, whereby the ion beam produced by the subsystem can be used in focused ion-beam applications.

2. The system of claim 1 wherein the population of atoms is comprised of atoms selected from the group of lithium, sodium, potassium, rubidium, cesium, magnesium, calcium, strontium, barium, chromium, erbium, silver, ytterbium, mercury, helium, neon, argon, krypton, and xenon.

3. The system of claim 1 wherein the electric field created by the array of electrodes is between $10^4$ V/m and $2 \cdot 10^7$ V/m.

4. The system of claim 1 wherein the population of atoms has a temperature of less than 2 mK along at least two transverse axes.

5. The system of claim 1 wherein the population of atoms is provided by an atomic beam directed along an axis.

6. The system of claim 5 wherein the laser beam or the beams of radiation is comprised of exactly two beams oriented substantially at right angles to each other.

7. The system of claim 1 wherein the population of atoms is provided by atoms confined in a magneto-optical trap.

8. A method for resonantly ionizing atoms to produce ions for a photoionized gas ion source, comprising:

a) providing an electric field having a magnitude and a direction in a region of space;

b) providing a population of atoms having a photoionizing resonant frequency specific to said electric field in said region of space;

c) applying one or more beams of laser radiation to at least a portion of the atoms, said one or more beams of laser radiation tuned to a frequency that corresponds to said photoionizing resonant frequency, whereby said at least a portion of the atoms are excited from a ground state to a quasi-bound excited state that will subsequently ionize over time at a given rate, said laser beam or beams of radiation having a total photon energy less than a field-free ionization potential of said population of atoms;

d) thereby ionizing at least a portion of atoms;

e) accelerating the ions to form a beam in the direction of the provided electric field; and f) providing a vacuum chamber evacuated to less than about $10^{-6}$ millibar, said vacuum chamber configured to contain at least the population of atoms, at least a portion of the electrodes, the portion of the beams of laser radiation that overlap with said population of atoms, and the beam of ions, whereby the accelerated ions form a beam that can be used in focused ion-beam applications.

9. The method of claim 8 wherein the ionizing of at least the portion of the atoms includes photoionizing the atoms by employing a quasi-bound state, the state having a lifetime less than 10 μs.

10. The method of claim 8 wherein the ionizing of at least the portion of the atoms, the atoms having a field free ionization potential, imparts a recoil to said ions that is substantially less than would be imparted by tuning the laser radiation to supply a photo energy to each ionizing atom substantially equal to the electric field-free ionization potential.

11. The method of claim 8 wherein the ionizing of at least the portion of the atoms induces one or more electric multipole interactions in the population of atoms and ions that inhibits the excitation of at least some of the atoms via the photoionizing resonant frequency.

12. The method of claim 11 wherein the electric multipole interaction is substantially created by the interaction between dipole moments of two or more of the atoms.

13. The method of claim 11 wherein the electric multipole interaction is substantially created by the interaction between the electric field of the ion or ions and the dipole moment of at least one of the atoms.

14. The method in claim 8, further comprising substantially varying an intensity of said beam of laser radiation over a period of time.

15. A photoionization system comprising:

an electric field generator configured to generate a substantially controllable applied electric field having a magnitude and direction;

one or more radiation sources configured to produce one or more beams of radiation tuned to a frequency that corresponds to a photoionizing resonant frequency of a portion of a population of atoms specific to said applied electric field, whereby said at least a portion of the atoms are excited from a ground state to a quasi-bound excited state that will subsequently ionize over time at a given rate, to produce ions that are accelerated by the electric field so as to form at least one beam of ions; said laser beam or beams of radiation having a total photon energy less than a field-free ionization potential of said population of atoms, and a vacuum chamber configured to be evacuated to less than about $10^{-6}$ millibar and to contain at least some of the atoms, at least a portion of the electric field generator, the portion of the beams of radiation that overlap with the population of atoms, and the beam of ions so as to focus the ion beam.

16. The photoionization system of claim 15 wherein the one or more radiation sources are positioned to produce beams of laser radiation angled relative to one another.

17. The photoionization system of claim 15, wherein the one or more radiation sources are configured to provide radiation for photoionizing at least some of the atoms by employing a quasi-bound state, the state having a lifetime less than 10 μs.

18. The photoionization system of claim 15 wherein the one or more radiation sources are configured to ionize at least some of the atoms, the atoms having a field free ionization potential, to impart a recoil to said ions that is substantially less than would be imparted by tuning the one or more radiation sources to supply a photo energy to each ionizing atom substantially equal to the electric field-free ionization potential.

19. The photoionization system of claim 15 wherein the field generator includes a plurality of electrodes that cooperate to produce the applied electric field.

* * * * *